(12) United States Patent
Sansoucy

(10) Patent No.: US 7,943,077 B2
(45) Date of Patent: May 17, 2011

(54) METHOD FOR MANUFACTURING A CATHETER HAVING A SEPARATED TIP CONFIGURATION

(75) Inventor: Michael R. Sansoucy, Wrentham, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/823,322

(22) Filed: Jun. 25, 2010

(65) Prior Publication Data

US 2010/0327492 A1    Dec. 30, 2010

Related U.S. Application Data

(60) Provisional application No. 61/221,702, filed on Jun. 30, 2009.

(51) Int. Cl.
*B29C 45/36* (2006.01)

(52) U.S. Cl. .......... 264/328.1; 264/328.7; 264/334; 249/64

(58) Field of Classification Search ........... 264/328.1, 264/328.7, 334, 335, 338, 336; 249/64; 425/577
See application file for complete search history.

(56) References Cited

U.S. PATENT DOCUMENTS

| | | | | |
|---|---|---|---|---|
| 3,901,965 A * | 8/1975 | Honeyman, III | .......... | 264/328.1 |
| 4,284,459 A * | 8/1981 | Patel et al. | .......... | 156/245 |
| 4,956,141 A * | 9/1990 | Allen et al. | .......... | 264/297.2 |
| 5,240,397 A * | 8/1993 | Fay et al. | .......... | 425/145 |
| 5,470,522 A * | 11/1995 | Thome et al. | .......... | 264/328.1 |
| 5,683,644 A * | 11/1997 | Peterson | .......... | 264/318 |
| 6,444,157 B1 * | 9/2002 | Miyajima | .......... | 264/511 |
| 6,984,119 B1 * | 1/2006 | Hickman et al. | .......... | 425/503 |
| 2003/0153898 A1 | 8/2003 | Schon et al. | | |
| 2009/0143767 A1 | 6/2009 | Fentress et al. | | |

OTHER PUBLICATIONS

International Search Report dated Aug. 11, 2010 for copending International Application No. PCT/US10/40295.

\* cited by examiner

*Primary Examiner* — Jill L Heitbrink
(74) *Attorney, Agent, or Firm* — Thomas M. Johnston, Esq.

(57) ABSTRACT

A method for manufacturing a separated tip catheter includes the following steps: positioning first and second cores in a cavity of a mold, the cavity having a substantially elongated shape and including a first end portion and a second end portion, wherein the first and second cores are oriented substantially parallel to each other; placing a sheet of material having a higher melting temperature than a molding material across the first end portion of the cavity; and injecting the molding material into the cavity of the mold.

19 Claims, 4 Drawing Sheets

METHOD FOR MANUFACTURING A CATHETER HAVING A SEPARATED TIP CONFIGURATION

This application claims priority to U.S. Provisional Application Ser. No. 61/221,702 filed on Jun. 30, 2009. The entire contents of which is incorporated herein by reference.

BACKGROUND

1. Technical Field

The present disclosure relates generally to methods for manufacturing catheters, and, in particular, methods for manufacturing catheters having a separated tip configuration.

2. Description of the Related Art

Catheters are flexible medical devices which facilitate the withdrawal and introduction of fluids from and to body cavities, ducts, and vessels. Catheter assemblies may have particular application in a hemodialysis procedure where blood is withdrawn from a blood vessel for treatment and subsequently returned to the blood vessel for circulation. Known hemodialysis catheters include multiple lumens, such as dual-lumen or triple-lumen catheters, which permit bi-directional fluid flow within the catheter whereby one lumen is dedicated for withdrawal of blood from a body vessel and the other lumen is dedicated for returning the treated blood to the vessel. During an exemplary hemodialysis procedure, a multiple lumen catheter is inserted into a body and blood is withdrawn through an arterial lumen of the catheter. The removed blood is directed to a hemodialysis unit which dialyzes, or purifies, the blood to remove waste and toxins from the blood. The dialyzed blood is returned to the patient through a venous lumen of the catheter.

Catheters can be manufactured using a variety of techniques including, for example, extrusion. For example, some catheters are formed by extruding a molten polymer through an extrusion die capable of producing a catheter having a uniform outer diameter. However, the addition of separated tip configurations to catheters has complicated these manufacturing techniques.

Accordingly, a continuing need exists in the medical arts for a simpler, cost effective method for manufacturing a catheter having a separated tip configuration.

SUMMARY

The present disclosure relates to methods for manufacturing catheters having separated tip configurations. In one embodiment, this method includes the steps of: positioning first and second cores in a cavity of a mold, the cavity having a substantially elongated shape and including a first end portion and a second end portion, wherein the first and second cores are oriented substantially parallel to each other; placing a sheet of material having a higher melting temperature than a molding material across the first end portion of the cavity; and injecting the molding material into the cavity of the mold. In one embodiment, the sheet is maintained in tension while injecting the molding material into the cavity of the mold. The sheet may be positioned between the first and second cores.

Each of the first and second cores may define a longitudinal bore and one or more pores. The cores may be covered with, for example, a covering film prior to injecting the molding material to restrict the flow of molding material through or into the one or more pores. A media may be supplied along the sheet to facilitate removal of the sheet and/or first and second cores from the mold. The mold may include first and second halves which collectively define the cavity. The first and second sides of the mold may be separated after the molding material has cooled. At least one of the first and second cores may be heated before injecting the molding material into the mold. The mold may be heated before injecting the molding material into the cavity of the mold.

The first and second cores may be held with one or more retractable pin assemblies to minimize deflection of the first and second cores prior to injecting the molding material into the mold. Each retractable pin assembly includes one or more retractable pins movable transversely relative to the cavity of the mold between a retracted position outside of the cavity of the mold and an engaged position for engaging the first core or the second core. At least one retractable pin may be positioned between the first and second cores. At least one retractable pin engages an outer surface of the first core or second core. In one embodiment, each retractable assembly has three retractable pins oriented substantially parallel relative to each other. The method may further includes moving at least one of the three retractable pins into a gap defined between the first and second cores. In one embodiment, the method may further include engaging the one or more retractable pin to an outer surface of the first core or second core.

A viscosity modifier may be added to the molding material. The molding material may be polyurethane or a viscous polyurethane slurry.

The present disclosure further relates to an alternate method for manufacturing a catheter having a separated tip configuration. This method includes melting a molding material; inserting first and second cores into a cavity of a mold, the cavity having a geometry for forming an outer surface of a catheter and including a first end portion and a second end portion, the first and second cores having a geometry for defining lumens in the catheter; placing a sheet of material having a higher melting temperature than the molding material across the first end portion of the cavity and between the first and second cores; injecting the molding material into the cavity of the mold; and maintaining the sheet in tension during the step of injecting the molding material into the cavity of the mold. The molding material may be polyurethane. The first and second cores may be positioned in a parallel orientation relative to each other.

The first and second cores may be hold with one or more retractable pin assemblies to minimize deflection of the first and second cores prior to injecting the molding material into the mold. Each retractable pin assembly includes one or more retractable pins movable transversely relative to the cavity of the mold between a retracted position outside of the cavity of the mold and an engaged position for engaging the first core or the second core. At least one retractable pin may be positioned between the first and second cores. At least one retractable pin engages an outer surface of the first core or second core. In one embodiment, each retractable assembly has three retractable pins oriented substantially parallel relative to each other. The method may further include moving at least one of the three retractable pins into a gap defined between the first and second cores. In one embodiment, the method may further include engaging the one or more retractable pins to an outer surface of the first core or the second core.

BRIEF DESCRIPTION OF THE DRAWINGS

Various embodiments of the presently disclosed catheters and manufacturing assemblies and methods are described herein with references to the accompanying drawings, wherein.

DETAILED DESCRIPTION OF THE EMBODIMENTS

Figure 1:
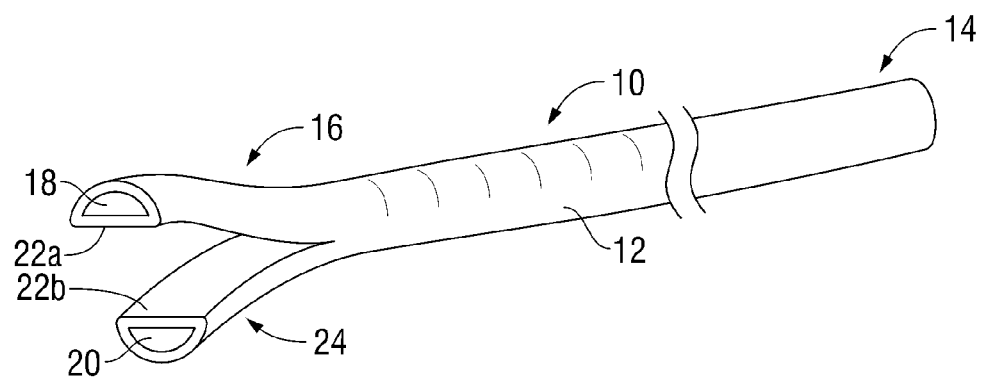
FIG. 1 is a perspective view of a catheter having a separated tip configuration.

Embodiments of the presently disclosed manufacturing assemblies and methods will now be described in detail with reference to the drawings wherein like reference numerals identify similar or identical elements in each of the several views. In the discussion that follows, the term "proximal" or "trailing" will refer to the portion of a structure that is closer to a user, while the term "distal" or "leading" will refer to the portion of the structure that is farther from the user. As used herein, the term "subject" refers to a human patient or animal. The term "clinician" refers to a doctor, nurse or other care provider and may include support personnel.

FIG. 1 illustrates a catheter 10 having a separated tip configuration. As used herein, separated tip configuration means that the distal end of the catheter includes first and second tip members which are disconnected such that they can move or be moved in relation to each other. In general, catheter 10 includes an elongate body 12 having a proximal end portion 14 and a distal end portion 16. Elongate body 12 defines first and second lumens 18, 20 which extend the length of elongate body 12. In the depicted embodiment, elongate body 12 has a cylindrical shape and each lumen 18, 20 features a semi-circular or D-shaped cross-section. Alternatively, elongate body 12 and lumens 18, 20 may have any suitable shape or configuration. Elongate body 12 further includes a septum (not shown) dividing first and second lumens 18, 20. Catheter 10 includes a separated tip portion 24 adjacent distal end portion 16 of catheter 10 which includes a first tip member 22a and a second tip member 22b separated from each other. The present disclosure describes a manufacturing process to make catheter 10, as shown in FIG. 1.

Catheter 10 may be made of any suitable biocompatible material. In certain embodiments, catheter 10 is formed of polyurethane. To be even more specific, catheter 10 can be formed of aliphatic or aromatic polyurethane. However, catheter 10 may be made of any suitable polymer such as polyamides, polyesters, polyolefins, fluoropolymer (such as fluorinated ethylene propylene (FEP), polytetrafluoroethylene (PTFE), perfluoroalkoxy (PFA), polyvinylidene fluoride (PVDF)), polyvinyl chloride (PVC), silicones (poly-dimethyl Siloxane), and so forth, as well as combinations including at least one of the foregoing (i.e., polymer blends, copolymers, alloys and so forth).

A number of manufacturing assemblies and procedures may be employed to make catheter 10. For example, catheter 10 may be made by injection molding which is a manufacturing process for forming objects, utilizing thermoplastic or thermoset plastics, metals, or ceramic materials, by heating the molding material and injecting it into a mold. During injection molding, a molding material or resin is shaped to form a desired part or object. Most polymers, including thermoplastics, thermosets, and elastomers, may be used as molding materials.

With reference to FIGS. 2-4B, a manufacturing assembly 1000 generally includes a mold 100 or 200 (FIGS. 4A and 4B), a core assembly 116, and a sheet or film 102 for bisecting a molding material 140 within mold 100 or 200. Core assembly 116 is received within mold 100 or 200 and facilitates the formation of first and second lumens 18, 20 of catheter 10 (FIG. 1) during the manufacturing process. As discussed in further detail below, sheet 102 is configured to divide molding material 140 inside mold 100 or 200 to form separated tip portion 24 of catheter 10 (FIG. 1).

Figure 2:
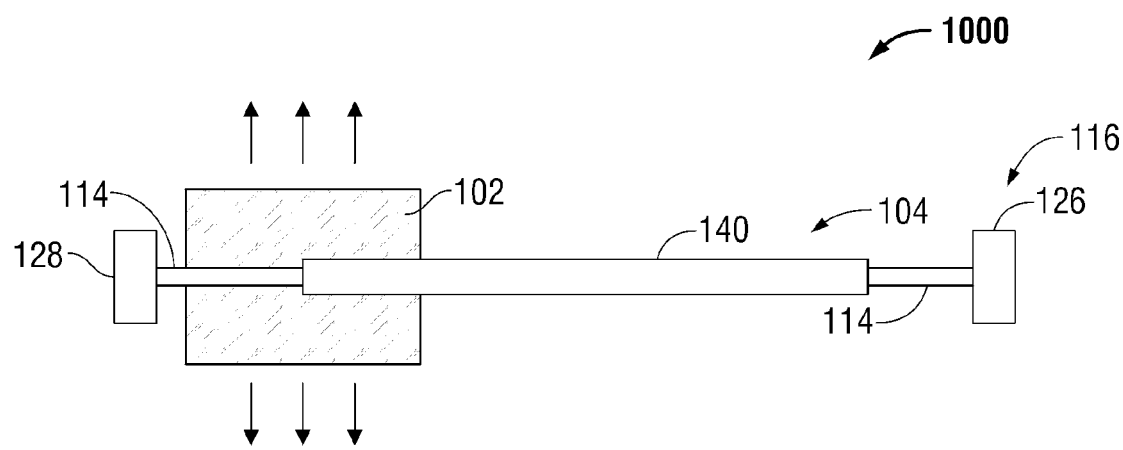
FIG. 2 is a top view of a manufacturing assembly for making the catheter shown in FIG. 1.
Figure 3:
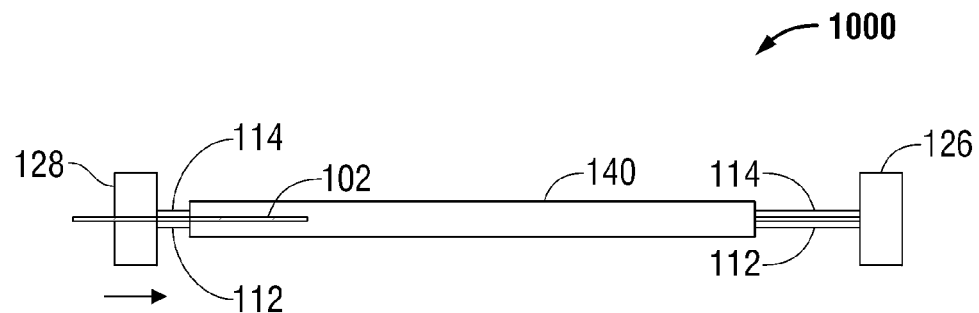
FIG. 3 is a side view of the manufacturing assembly of FIG. 2.
Figure 4A:
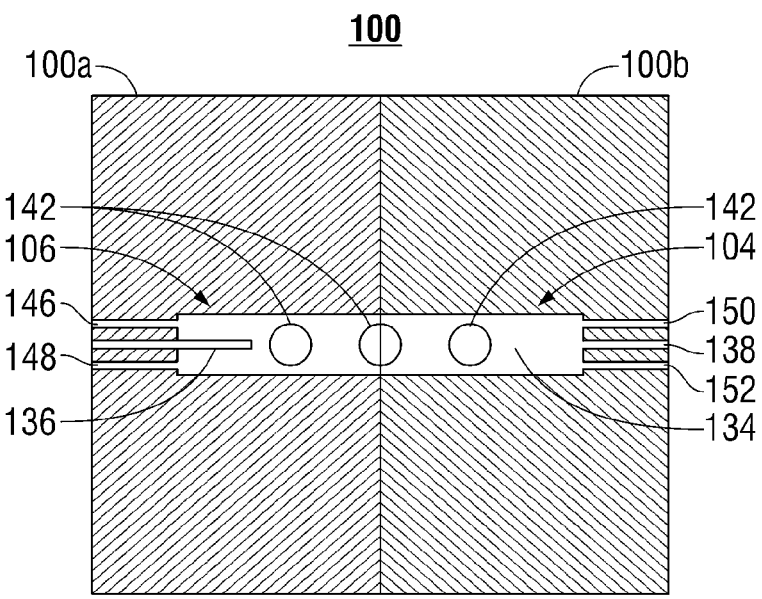
FIG. 4A is a side cross-sectional view of a mold according to an embodiment of the manufacturing assembly shown in FIG. 2.

FIG. 4A depicts an embodiment of a mold 100 including first and second halves 100a, 100b. In the depicted embodiment, first and second halves 100a, 100b are substantially symmetrical. Alternatively, first and second halves 100a, 100b may be asymmetrical. Irrespective of their symmetry (or lack thereof), first and second halves 100a, 100b of mold 100 collectively define a cavity 134 for holding molding material 140 (FIGS. 2 and 3). Cavity 134 has an elongate shape and defines a geometry capable of forming the outside surfaces of catheter 10. In one embodiment, cavity 134 has a substantially cylindrical shape although other cavity shapes are envisioned, e.g., oval, square, rectangular, etc. Cavity 134, which includes a first end portion 104 and a second end portion 106, is configured to receive molding material 140 and cores 112, 114 (FIG. 3) of core assembly 116. In this embodiment, first end portion 104 of cavity 134 is located in second half 100b of mold 100 and second end portion 106 of cavity 134 is located in first half 100a of mold 100. First half 100a of mold 100 defines a slot 136 disposed in communication with second end portion 106 of cavity 134. Slot 136 is dimensioned to receive sheet 102 (FIG. 2) during the manufacturing process. Second half 100b of mold 100 includes a sprue 138 for allowing passage of molten molding material 140 (FIG. 2) into cavity 134. In the depicted embodiment, sprue 138 is disposed in fluid communication with first end portion 104 of cavity 136. Sprue 138, however, may be located on any portion of mold 100 as long as its position permits fluid communication between cavity 134 and a source of molten molding material.

With continued reference to FIG. 4A, first half 100a of mold 100 defines first and second bores 146, 148, which are oriented substantially parallel to each other and are each dimensioned to receive first and second cores 112, 114 (FIG. 5), respectively. Each bore 146, 148 is disposed in communication with the second end portion 106 of cavity 134. Second half 100b of mold 100 defines first and second bores 150, 152, which are oriented substantially parallel to each other and dimensioned to receive first and second cores 112, 114 (FIG. 5), respectively. Each bore 150, 152 is disposed in communication with first end portion 104 of cavity 134.

Figure 4B:
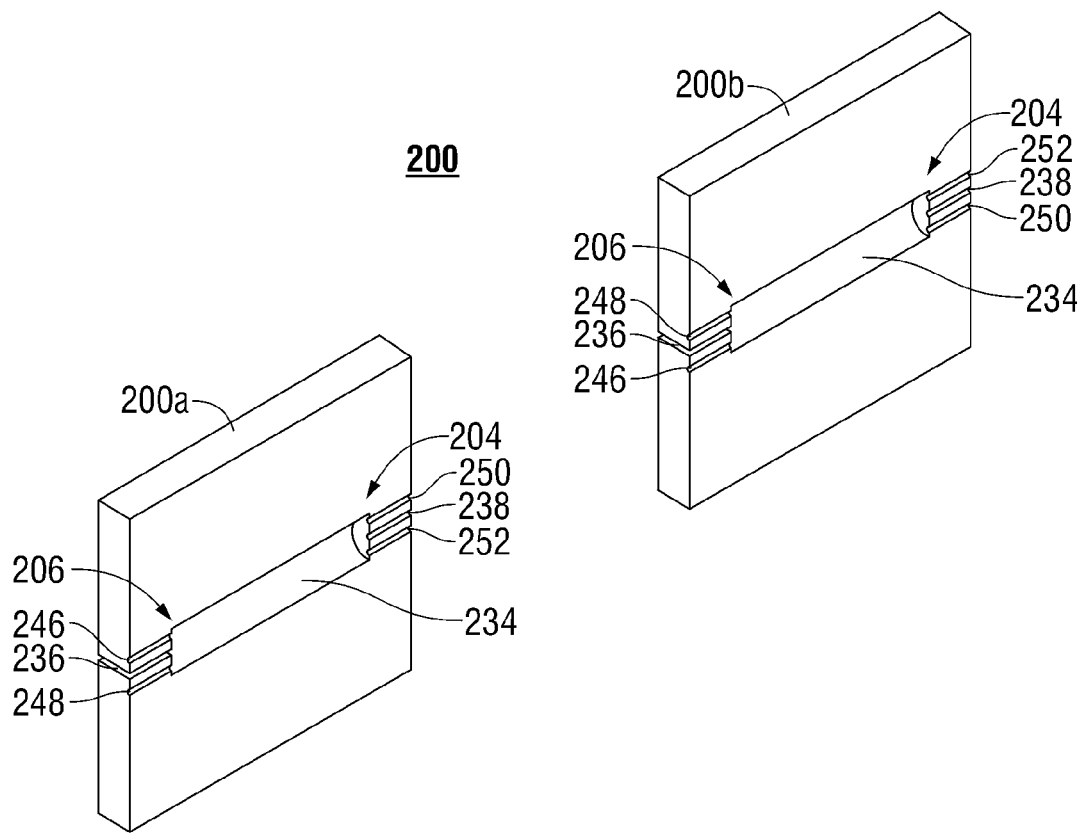
FIG. 4B is a perspective view of a mold according to an embodiment of the manufacturing assembly shown in FIG. 2.

FIG. 4B shows another embodiment of a mold 200 including first and second halves 200a, 200b. In the depicted embodiment, first and second halves 200a, 200b of mold 200 are substantially symmetrical although it is envisioned that first and second halves 200a, 200b may be asymmetrical. First and second halves 200a, 200b of mold 200 collectively define a cavity 234 for holding molding material 140 (FIGS.

2 and 3). Cavity 234 has an elongate shape and defines a geometry capable of forming the outside surfaces of catheter 10. In one embodiment, cavity 234 has a substantially cylindrical shape although other shapes are envisioned. Cavity 234 is configured to receive molding material 140 and cores 112, 114 (FIG. 3) of core assembly 116. In this embodiment, first and second halves 200a, 200b of mold 200 jointly define a first end portion 204 and a second end portion 206 of cavity 234. Mold 200 further defines a slot 236 disposed in communication with second end portion 106 of cavity 234. Slot 236 is dimensioned to receive sheet 102 (FIG. 2) during the manufacturing process. In addition, mold 200 defines a sprue 238 disposed in fluid communication with cavity 236 for allowing passage of molten molding material 140 (FIG. 2) into cavity 234. Although FIG. 4B shows sprue 238 positioned adjacent first end portion 204 of cavity 236, sprue 238 may be located on any portion of mold 200 as long as its position permits fluid communication between cavity 234 and a source of molten molding material.

With continued reference to FIG. 4B, first and second halves 200a, 200b of mold 200 together define first and second bores 246, 248, which are oriented substantially parallel to each other and positioned adjacent second end portion 206 of cavity 234. First and second bores 246, 248 are each dimensioned to receive first and second cores 112, 114 (FIG. 5) and are each disposed in communication with cavity 234. First and second halves 200a, 200b of mold 200 also define third and fourth bores 250, 252, which are oriented substantially parallel to each other and positioned adjacent first end portion 204 of cavity 234. Third and fourth lumens 250, 252 are each dimensioned to receive first and second cores 112, 114 (FIG. 5) and each are disposed in communication with cavity 234.

As seen in FIGS. 2-5, core assembly 116 includes first and second cores 112, 114 for forming lumens 18, 20 of catheter 10 and first and second core supporting structures 126, 128. Although not shown, the first and second cores can be integrally formed or otherwise connected at one end. In one embodiment, first and second cores 112, 114 are fixedly attached to at least one of the first and second core supporting structures 126, 128 and releasably coupled to the other of the first and second core supporting structures 126, 128. In operation, an operator can place the first and second cores 112, 114 into cavity 134 or 234. Yet further, the core supporting structures may be capable of imparting a tensile force on the first and second cores 112, 114 which could limit deflection of the cores when the material 140 is injected into the cavity 134, 234. Yet further, the core supporting structures may be capable of imparting a tensile force on the first and second cores 112, 114 which could limit deflection of the cores when the material 140 is injected into the cavity 134, 234.

Figure 5:
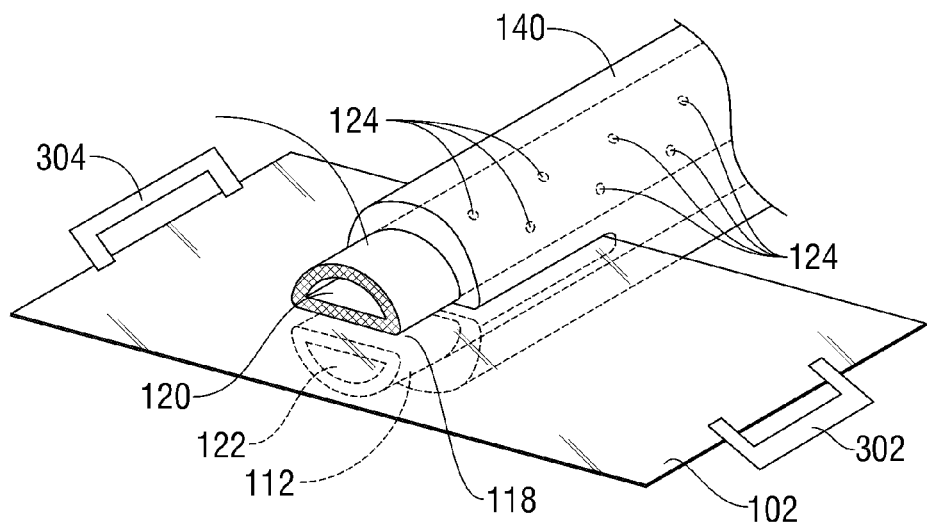
FIG. 5 is an enlarged perspective view of a first end portion of the manufacturing assembly shown in FIG. 2.

As shown in FIG. 5, first and second cores 112, 114 define longitudinal bores 120, 122, respectively, and may include pores 124 for allowing passage of a liquid or gaseous media therethrough. Pores 124 may be formed by laser cutting, drilling or other known techniques. In operation, the operator may force liquid media through longitudinal bores 120, 122 and pores 124 to facilitate separation of cores 112, 114 from the cooled molding material 140 after the injection molding process. A covering film (not shown) may be placed over first and second cores 112, 114 during the molding process to restrict molten molding material 140 (FIG. 5) from entering into or flowing through pores 124 during injection molding. For example, the covering film could be a heat shrink tubing that has been applied over the first and second cores 112, 114 individually prior to molding. Yet further, the covering film itself may enable the removal of the first and second cores 112, 114 from the molding material 140. For example, floropolymer shrink tube (e.g., FEP) may be assembled over the first and second cores 112, 114 to enable the cores to be removed from the molding material 140. In addition, first and second cores 112, 114 together define a gap 118 (FIG. 5) dimensioned to receive sheet 102 to form separated tip portion 24 of catheter 10 (FIG. 1). Further still, it should be apparent to one skilled in the art of polymer injection molding and materials that additional methods of removing the first and second cores 112, 114 are available. For example, molding material 140 may be swelled in a solvent, or the molding material may be disposable such as utilizing an acetal extrusion that could be elongated and necked-down thereby reducing its outer circumference to easily remove the cores.

Referring to FIGS. 2 and 3, in one embodiment, manufacturing assembly 1000 includes slides 302, 304 schematically shown in FIG. 5 which are attached to sheet 102. During the injection molding process, slides 302, 304 maintain sheet 102 in tension. In one exemplary method, a slide (302 or 304) is attached to each side of sheet 102 and slides 302, 304 are moved in opposite directions to create tension in sheet 102. Sheet 102 is made of any material suitable for bisecting the molding material which has a higher melting point than the molding material. Slides 302, 304 may be operatively supported on the mold 100 or 200.

Figure 6:
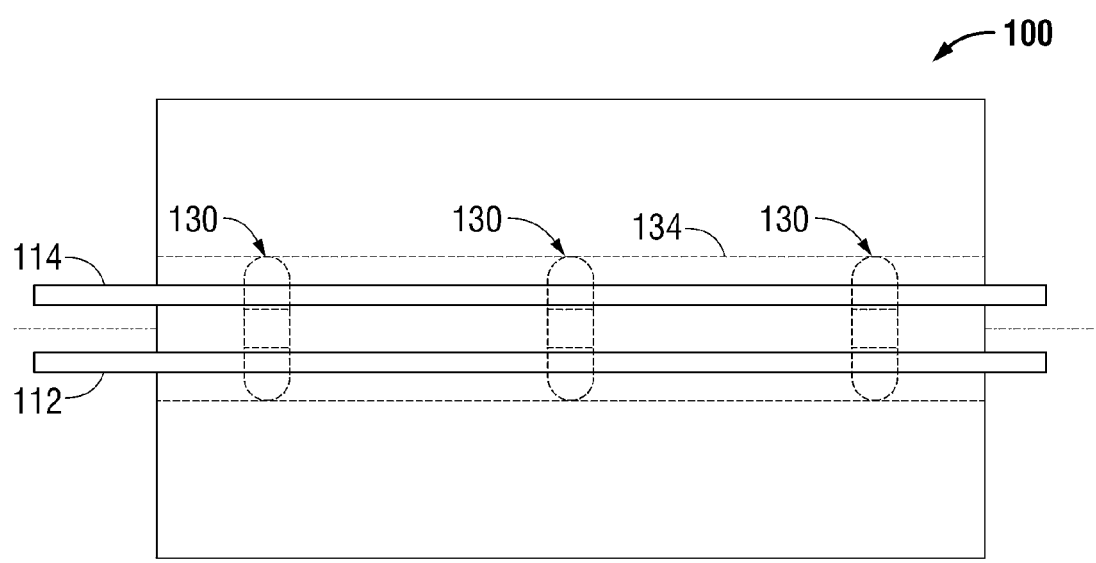
FIG. 6 is a side view of manufacturing assembly of FIG. 2, showing retractable pins assemblies.
Figure 7:
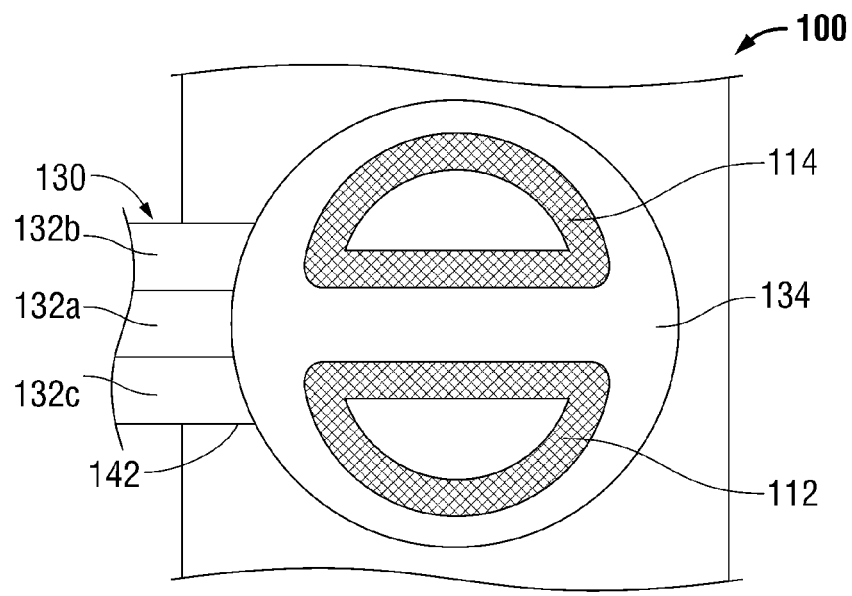
FIG. 7 is a front view of the manufacturing assembly of FIG. 2, showing retractable pins in a retracted position.
Figure 8:
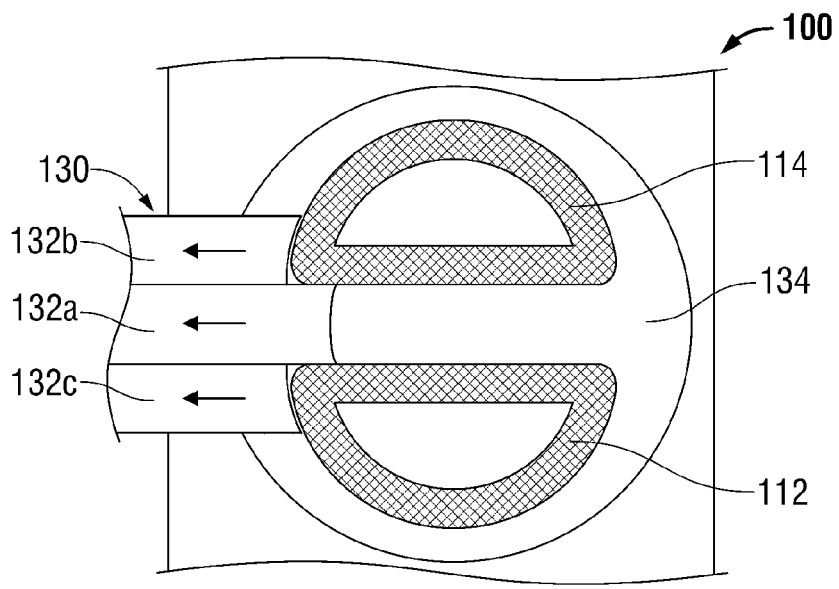
FIG. 8 is a front view of the manufacturing assembly of FIG. 2, showing the retracted pins in an engaged position.

As seen in FIGS. 6-8, manufacturing assembly 1000 may include at least one retractable pin assembly 130 including retractable pins 132 configured to move transversely with respect to cores 112, 114 between a retracted position (FIG. 7) and an engaged position (FIG. 8). In one embodiment, retractable pin assembly 130 may be operatively coupled to first half 100a of mold 100 (FIG. 4). Alternatively, retractable pin assembly 130 may be operatively coupled to second half 100b of mold 100. Mold 100 includes one or more bores 142 dimensioned to receive pins 132 of each retractable pin assembly 130. Each bore 142 of mold 100 leads to cavity 134 and is oriented transversely relative to cavity 134. When retractable pin assembly 130 is in the retracted position, retractable pins 132 surround cavity 134 or 234 so as to form the cavity surface and do not engage first and second cores 112, 114. Alternatively, retractable pins 132 are positioned outside cavity 134 or 234 when placed in the retracted position. When retractable pin assembly 130 is in the engaged position, retractable pins 132 are at least partially positioned inside cavity 134 or 234 of mold 100 or 200 and at least one retractable pin 132 engages first and second cores 112, 114 to inhibit or prevent deflection of first and second cores 112, 114 during the manufacturing process. In the embodiment shown in FIGS. 6-7, manufacturing assembly 1000 includes three retractable pin assemblies 130. It is envisioned, however, that manufacturing assembly 1000 may include more or fewer retractable pin assemblies 130. It should be apparent to one skilled in the art that the plurality of pins and/or the use of pin assemblies (i.e., one pin may be utilized) can be modified in any manner to reduce deflection of the first and second cores 112, 114.

In the embodiment shown in FIGS. 7 and 8, each retractable pin assembly 130 includes three pins 132. One retractable pin 132a is positioned in gap 118 (FIG. 8) in its advanced position between first and second cores 112, 114 to maintain separation between first and second cores 112, 114 during the injection molding process. Another pin 132b is adapted to engage an outer surface of first core 114. A further pin 132c is configured to engage an outer surface of second core 112. All retractable pins 132 can be positioned adjacent one another to provide stability to retraction pin assembly 130.

Figure 9:
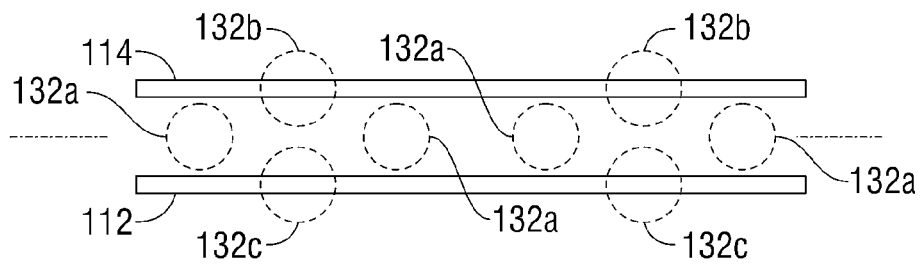
FIG. 9 is a side view of a manufacturing assembly of FIG. 2, showing retractable pins according to another embodiment of the present disclosure.

As seen in FIG. 9, manufacturing assembly 1000 (FIG. 2) may include retractable pins 132a, 132b, 132c that are not aligned with each other. While FIG. 9 shows eight retractable pins 132a-c, manufacturing assembly 1000 (FIG. 2) may include fewer or more retractable pins. In the embodiment shown in FIG. 9, retractable pins 132a are configured to move relative to mold 100 or 200 between a retracted position to form the cavity surface of mold 100 or 200 and an engaged positioned to support first and second cores 112, 114. In the engaged position, retractable pins 132a are located in gap 118 (FIG. 5) between first and second cores 112, 114 to maintain separation between first and second cores 112, 114 during the injection molding process. Retractable pins 132b are configured to move relative to mold 100 or 200 between a retracted position to form the cavity surface of mold 100 or 200 and an engaged position to engage the outer surface of first core 114. Retractable pins 132c are adapted to move relative to mold 100 or 200 between a retracted position to form the cavity surface of mold 100 or 200 and an engaged position to engage the outer surface of second core 112.

In one embodiment, manufacturing assembly 1000 may include a controller and/or sensor (not shown) capable of mechanically actuating, e.g., advancing and/or retracting, retractable pin assemblies 130 when molding material 140 is injected into cavity 134 or 234 of mold 100 or 200. In this embodiment, retractable pins 132a-c of retractable pin assembly 130 are automatically moved from the retracted position to the engaged position when the molding material 140 is injected into cavity 134 or 234 of mold 100 or 200. It is also envisioned that retractable pins 132a-c can be retracted after at least a portion of the molding material 140 has be injected into the mold 100 or 200 however prior to the point at which molding material 140 can sufficiently flow to fill in the void created by the retraction of the retraction pins 132a-c. In one example, retraction pins 132a-c can be retracted when the mold 100 or 200 is approximately 95% full of molding material 140, such that the pins are retracted just prior to "pack out", wherein "pack out" refers to the point at which the mold is approximately 99% full and additional pressure is exerted on the molten molding material 140 to completely fill cavity 134.

Retractable pins 132 may leave protrusions, voids or witness marks in the surface of catheter 10. However, molding material 140 may be subjected to secondary processes to remove these protrusions, voids or witness marks. For example, the manufacturer may trim a protrusion close to the surface of catheter 10 and place heat shrink tubing (not shown) around molding material 140 before removing first and second cores 112, 114 from molding material 140 but after removing molding material 140 from mold 100 or 200. Heat can be applied to the heat shrink tubing that causes the protrusion to flow, forming a smooth catheter 10 surface and/or fill the voids or witness marks created by retractable pins 132. Alternatively, the manufacturer may run catheter 10 through a heated die to remove the holes or witness marks created by retractable pins 132 after removing the finished product from mold 100 or 200. In one exemplary process, catheter 10 can be drawn through a heated orifice comprising a non-stick surface, wherein as catheter 10 contacts the surface of the heated orifice, the outermost surface of catheter 10 is heated causing the molding material 140 to soften and ultimately flow. The result of this process is a smooth outer surface on catheter 10, wherein the voids or witness marks have been smoothed out and/or covered.

In use of manufacturing assembly 1000, a manufacturer secures first and second halves 100a, 100b or 200a, 200b of mold 100 or 200 together using, for example, the clamp of an injection molding machine (See FIGS. 4A and 4B). While the first and second mold halves 100a, 100b or 200a, 200b of mold 100 or 200 are separated, the first and second cores 112, 114 can be placed into cavity 134 or 234 of mold 100 or 200, respectively. In addition, retractable pin assemblies 130 are moved to the engaged position so that retractable pins 132 are positioned within cavity 134 or 234. (See FIG. 8). When retractable pin assemblies 130 are positioned in the engaged position, at least one retractable pin 132 engages first and second cores 112, 114 and prevents or at least minimizes the degree of deflection of first and second cores 112, 114. Next, sheet 102 is inserted in a second end portion 106 or 206 of cavity 134 through slot 136 or 236 of mold 100 or 200, respectively, to create a division in the second end portion of the cavity. (See FIGS. 1, 4A, 4B, and 5). The first and second mold halves 100a, 100b or 200a, 200b of mold 100 or 200 are then brought together, wherein such action secures the first and second cores 112, 114 as well as causes slides 302, 304 to impart tension on sheet 102, as seen in FIG. 5.

Having sufficient heat applied to molding material 140 such that it can flow when acted upon by pressure, the heated molding material 140 is injected into cavity 134 or 234 of mold 100 or 200 through sprue 138 or 238, respectively. (See FIGS. 4A and 4B). When the molten molding material 140 is injected into cavity 134 or 234, molding material 140 will fill the cavity 134 or 234 along the elongate body 12 and bisected by sheet 102 at the second end portion 106 or 206 of cavity 134 or 234. To minimize deflection of the first and second cores 112, 114, high melt temperatures (e.g., 415° F. for an aliphatic polyurethane) and low injection pressures (e.g., 500 psi injection pressure at injection unit) can be employed during the injection molding process. Further, one or more gates can be utilized to optimize filling of the cavity during injection to minimize core deflection. In one embodiment, core assembly 116 and/or mold 100 or 200 are heated in an oven before injecting molding material 140 into cavity 134 to minimize deflection of first and second cores 112, 114. It is envisioned that core assembly 116 and mold 100 or 200 may be heated using any suitable process or means.

Next, the molten molding material 140 is allowed to remain in the cavity 134 or 234 until the molding material 140 has reached a temperature that cavity 134 or 234 can be opened and the catheter 10 can be ejected or otherwise removed from cavity 134 or 234. A suitable temperature will be below the melt temperature (Tm) of the material. The cavity 134 or 234 is generally internally cooled with a liquid media to expedite cooling. Thereafter, the manufacturer removes first and second cores 112, 114 from cavity 134 and unclamps first and second halves 100a, 100b or 200a, 200b of mold 100 or 200 to release the finished product, i.e., catheter 10. (See FIGS. 4A and 4B). Optionally, a release agent (e.g., silicone) can be applied to the first and second cores 112, 114 to ease removal from the catheter 10. Further a release agent can be applied to sheet 102 and/or to cavity 134 or 234 to lubricate first and second cores 112, 114 and aid in the removal of the finished product from cavity 134 or 234 of mold 100 or 200. Further, a media, such as gas or liquid, may be forced into bores 120, 122 and pores 124 of first and second cores 112, 114 to aid in the separation of first and second cores 112, 114 from molding material 140. (See FIG. 5).

It is contemplated that viscosity modifiers may be added to the molding material to reduce the viscosity of the molding material, thus further assisting in processing of the molding material. In certain embodiments, the manufacturer may also or separately employ solvents to reduce the viscosity. For example, a viscous molding slurry may be formed by mixing polyurethane and methyl ethyl ketone, which can be injected into mold 100 or 200 to minimize deflection of first and second cores 112, 114 and minimize the use of heat during the injection molding. In such an example, heat may not be required to achieve fluid-flow of the molding material. Yet further, retractable pin assembly 130 may not be required in applications employing a slurry less force may be required to provide fluid flow of the slurry compared to a molten molding material 130.

Although the specific features of the disclosure are shown in some drawings and not in others, this is for convenience only as each feature may be combined with any or all of the other features in accordance with the disclosure.

It will be understood that various modifications may be made to the embodiments of the presently disclosed clamping assemblies. Therefore, the above description should not be construed as limiting, but merely as exemplifications of embodiments. Those skilled in the art will envision other modifications within the scope and spirit of the present disclosure.

What is claimed is:

1. A method for manufacturing a catheter having a separated tip configuration, comprising the steps of:
   positioning first and second cores in a cavity of a mold, the cavity having a substantially elongated shape and including a first end portion and a second end portion, wherein the first and second cores are oriented substantially parallel to each other;
   placing a sheet of material having a higher melting temperature than a molding material across the first end portion of the cavity;
   tensioning the sheet of material as the mold is closed; and
   injecting the molding material into the cavity of the mold.

2. The method according to claim 1, wherein the step of placing the sheet across the first end portion of the cavity includes positioning the sheet between the first and second cores.

3. The method according to claim 1, wherein the first and second cores are connected to each other and wherein the step of positioning the first and second cores in the cavity of the mold further includes simultaneously positioning the first and second cores in the cavity of the mold.

4. The method according to claim 1, wherein each of the first and second cores defines a longitudinal bore and one or more pores, and the method further includes the step of injecting a fluid through the longitudinal bores and the one or more pores to facilitate separation of the first and second cores from the molding material.

5. The method according to claim 4, further including the step of covering the pores with a covering film prior to the step of injecting the molding material to restrict the flow of molding material through the one or more pores.

6. The method according to claim 1, further comprising the step of applying a release agent to the first and second cores to ease removal of the first and second cores from the molding material.

7. The method according to claim 1, further comprising the step of applying tension to at least one of the first core or the second core to minimize deflection of the first core or the second core prior to the step of injecting the molding material into the mold.

8. The method according to claim 1, further comprising the step of heating at least one of the first and second cores before injecting the molding material into the mold.

9. The method according to claim 1, further comprising the step of holding the first and second cores with one or more retractable pins to minimize deflection of the first and second cores prior to the step of injecting the molding material into the mold.

10. The method according to claim 9, further comprising the step of moving the one or more retractable pins relative to the cavity of the mold between a retracted position and an engaged position engaged with the first core or the second core.

11. The method according to claim 10, wherein at least two of the one or more retractable pins are not aligned with one another.

12. The method according to claim 10, wherein the step of holding the first and second cores with one or more retractable pins further includes moving the one or more retractable pins into engagement with an outer surface of the first core or second core.

13. The method according to claim 1, further comprising the step of reducing the viscosity of the molding material with solvents.

14. The method according to claim 1, wherein the molding material is selected from the group consisting of polyurethane and a viscous polyurethane slurry.

15. A method for manufacturing a catheter having a separated tip configuration, comprising the steps of:
   melting a molding material;
   inserting first and second cores into a cavity of a mold, the cavity having a geometry for forming an outer surface of a catheter and including a first end portion and a second end portion, the first and second cores having a geometry for defining lumens in the catheter;
   placing a sheet of material having a higher melting temperature than the molding material across the first end portion of the cavity and between the first and second cores;
   injecting the molding material into the cavity of the mold; and
   maintaining the sheet in tension during the step of injecting the molding material into the cavity of the mold.

16. The method according to claim 15, wherein the step of inserting the first and second cores into the cavity of the mold includes positioning the first and second cores in a substantially parallel orientation relative to each other.

17. The method according to claim 15, further comprising the step of holding the first and second cores with one or more retractable pins to minimize deflection of the first and second cores during the step of injecting the molding material into the mold.

18. The method according to claim 17, wherein the step of holding the first and second cores with the one or more retractable pins further includes engaging the one or more retractable pins to an outer surface of the first core or second core.

19. The method according to claim 15, further comprising the step of applying tension to at least one of the first core or the second core to minimize deflection of the first core or the second cores prior to the step of injecting the molding material into the mold.

* * * * *